US00PP20905P2

(12) United States Plant Patent
Giesen

(10) Patent No.: US PP20,905 P2
(45) Date of Patent: Mar. 30, 2010

(54) *DIASCIA* PLANT NAMED 'DALA ORAN'
(50) Latin Name: *Diascia barberae*
Varietal Denomination: Dala Oran

(75) Inventor: Eric Giesen, Andijk (NL)
(73) Assignee: Goldsmith Seeds Europe B.V., Andijk (NL)

( * ) Notice: Subject to any disclaimer, the term of this patent is extended or adjusted under 35 U.S.C. 154(b) by 0 days.
(21) Appl. No.: 12/315,293
(22) Filed: Dec. 2, 2008
(51) Int. Cl.
*A01H 5/00* (2006.01)
(52) U.S. Cl. ..... Plt./425
(58) Field of Classification Search ..... Plt./425
See application file for complete search history.

*Primary Examiner*—June Hwu
(74) *Attorney, Agent, or Firm*—S. Matthew Edwards

(57) ABSTRACT

A new *Diascia* plant named 'Dala Oran' particularly distinguished by relatively large, deep orange flowers, medium to deep green foliage, strong branching and bushy, medium sized plant habit.

1 Drawing Sheet

Latin name of the genus and species of the plant claimed: *Diascia barberae.*

Varietal denomination: 'Dala Oran'.

BACKGROUND OF THE NEW PLANT

The present invention comprises a new *Diascia,* botanically known as *Diascia barberae,* and hereinafter referred to by the variety name 'Dala Oran.'

'Dala Oran' is a product of a planned breeding program. The new cultivar 'Dala Oran' has relatively large, deep orange flowers, medium to deep green foliage, strong branching and bushy, medium sized plant habit.

'Dala Oran' originated from a hybridization made in June 2005 in a controlled breeding program in Andijk, Netherlands. The female parent was an unpatented, proprietary *Diascia* plant designated 'DS05-103-4.' 'DS05-103-4' has a deeper salmon flower color and longer stems than 'Dala Oran.'

The male parent of 'Dala Oran' was an unpatented, proprietary *Diascia* plant designated 'DS05-115-1.' 'DS05-115-1' has a similar orange flower color, but smaller flowers and less deep green foliage than 'Dala Oran.'

The resulting seeds were sown in October 2005. 'Data Oran' was selected as one flowering plant within the progeny of the stated cross in January 2006 in a controlled environment in Andijk, Netherlands.

The first act of asexual reproduction of 'Dala Oran' was accomplished when vegetative cuttings were taken from the initial selection in the spring of 2006 in a controlled environment in Andijk, Netherlands.

Horticultural examination of plants grown from cuttings of the plant initiated in the spring of 2006 in Andijk, Netherlands, and continuing thereafter, has demonstrated that the combination of characteristics as herein disclosed for 'Dala Oran' are firmly fixed and are retained through successive generations of asexual reproduction.

'Dala Oran' has not been observed under all possible environmental conditions. The phenotype may vary significantly with variations in environment such as temperature, light intensity and day length.

No Plant Breeder's Rights for this cultivar have been applied so far. 'Dala Oran' has not been made publicly available more than one year prior to the filing of this application.

DESCRIPTION OF DRAWING

This new *Diascia* plant is illustrated by the accompanying photographic drawing which shows blooms, buds, and foliage of the plant in full color. The colors shown are as true as can be reasonably obtained by conventional photographic procedures.

The photograph, taken in Hillscheid, Germany in mid July 2007 shows 3 plants in a hanging basket and a close view of a flower.

The plants were 5–6 months old and were growing outdoors under rain protection.

DETAILED BOTANICAL DESCRIPTION

The measurements were taken in Hillscheid, Germany, mainly on April 5, using 8 week old greenhouse grown plants. Culture of these plants had started in early February 2008 with planting of rooted cuttings into 12 cm pots. The young plants were pinched once. Additional observations were made during the summer of 2008.

Color chart used: The Royal Horticultural Society Colour Chart (R.H.S.), 2001.

BRIEF SUMMARY OF INVENTION

The following observations, measurements, and comparisons describe plants grown indoors and outdoors in Andijk, Netherlands and in Hillscheid, Germany. The following traits have been repeatedly observed and are determined to be basic characteristics of the new variety. The combination of these characteristics distinguishes this *Diascia* as a new and distinct variety:

1. Relatively large, brilliant orange colored flowers
2. Floriferous and continuously flowering
3. Medium to deep green foliage, nearly round leaf shape
4. Densely branched and tight, compact plant habit with the inflorescences well above the foliage
5. About medium size, semi-upright to somewhat trailing, rounded habit.

COMPARISON WITH COMMERCIAL CULTIVARS

'Dala Oran' differs from the commercial cultivar 'Flying Colors Upright Coral' ('Diastis,' U.S. Plant Pat. No. 13,950) in that 'Dala Oran' has larger flowers and a taller plant habit than 'Diastis.' Additionally, the plant habit of 'Dala Oran' is more trailing, less upright.

'Dala Oran' differs from the commercial cultivar 'Diastusca' ('Flying Colors Orange,' U.S. Plant Pat. No. 17,723) in that 'Dala Oran' has a medium orange color, instead of an orange-red hue, deeper green foliage, and a rounded leaf shape.

TABLE 1

DIFFERENCES BETWEEN THE NEW VARIETY 'DALA ORAN' WITH SIMILAR VARIETIES

| | 'Dala Oran' | 'Diastis' (U.S. Plant Pat. No. 13,950) | 'Diastusca' (U.S. Plant Pat. No. 17,723) |
|---|---|---|---|
| Flower color | Deep orange, RHS 32A (indoors); RHS 32B (outdoors) | Salmon-orange, RHS 41C | Reddish-orange, RHS 34C to 35A |
| Plant and growth habit | Medium to tall | Distinctly taller, somewhat less tight than 'Dala Oran,' more upright directed stems | Roughly similar in size or slightly taller |
| Leaf shape | Cordate, relatively round | More ovate | More ovate (more elongate) |

Plant:

*Form, growth and habit.*—Bushy, tight, freely branching, semi-upright to semi-trailing.

*Height.*—15 cm (from top of soil) for 15 week old plants.

*Width (diameter).*—46 cm.

*Spread (including flowers).*—Approximately 20–25 cm, from the base of the main stem to the tips of the branches.

*Time to produce a finished flowering plant.*—About 8–10 weeks for a 12 cm pot.

*Outdoor plant performance.*—Plant in full sun; is free-flowering through the summer; has some heat tolerance; use in hanging-baskets. or mixed container planting.

*Time to initiate and develop roots.*—About 14 days, respective 21 days for a saleable, pinched young plant.

*Root description.*—Fibrous and freely branching.

Stem:

*Characteristics.*—Side branches are developed at almost every node.

*Stem length.*—Up to 25 cm, excluding the inflorescence.

*Diameter.*—0.2–0.3 cm in the middle part.

*Internode length.*—2.0–2.5 cm.

*Color.*—Mainly RHS 143C (light green), possibly a little anthocyanin at the base: RHS 182A.

*Texture.*—Appears smooth and glabrous.

Foliage:

*Arrangement.*—Single and opposite, decussate at non-flowering stems.

*Shape.*—Cordate to ovate.

*Apex.*—Broadly acute to obtuse.

*Base.*—Subcordate.

*Margin.*—Weakly crenate.

*Leaf length.*—2.5–2.7 cm.

*Leaf width.*—1.6–2.1 cm.

*Immature, leaf color, upper surface.*—RHS 137D to RHS 143A.

*Lower surface.*—Near RHS 138B.

*Mature, leaf color, upper surface.*—RHS 137B.

*Lower surface.*—RHS 138B.

*Venation type.*—Pinnate.

*Venation color.*—RHS 144B.

*Texture.*—Appears smooth and glabrous on both sides.

Petiole:

*Length.*—0.1–0.3 cm.

*Petiole width.*—0.2 cm.

*Petiole color.*—RHS 143C.

Inflorescence:

*Blooming habit.*—Continuous through the summer months.

*Quantity of inflorescences per plant.*—About 20–30.

*Type of inflorescence.*—Terminal raceme with flowers in an alternate arrangement at a distance of 0.5 to 1.0 cm.

*Number of flowers per inflorescence.*—Most often 5–7 open flowers, and additional buds.

*Lastingness of individual blooms on the plant.*—3–4 days.

*Fragrance.*—None.

*Inflorescent length.*—Most often 12–18 cm.

*Inflorescence diameter.*—3.2–3.8 cm.

Peduncle:

*Color.*—RHS 143B–C.

*Length.*—9–14 cm.

*Diameter.*—0.2 cm.

*Texture.*—Covered with very fine hair.

Flower:

*Corolla type and shape.*—Single, zygomorphic; salver-shape, 5 petals fused at the base, the two small upper petals mainly fused, two lateral lobes and a broad lower lobe; two short spurs emerge at the underside, formed by the lower ends of lateral and lower petals.

*Length.*—2.3–2.5 cm.

*Width.*—2.1–2.3 cm.

*Depth.*—0.4 cm.

*Color upper surface.*—Orange, RHS 32A (indoors), RHS 32B (outdoors).

*Color lower surface.*—Orange, RHS 33C or RHS 35B.

*Markings in the center.*—Reddish ring, RHS 47B to RHS 50B; upper petals have a yellow patch, RHS 13B, at the base.

Petal (lobes):

*Apex.*—Rounded.

*Base.*—Fused.

*Margin.*—Entire.

*Texture.*—Smooth, glabrous on both sides.

*Upper lobes, length (from the corolla opening).*—0.6 cm.

*Upper lobes, width (joint).*—1.2 cm.

*Lateral lobes, length (from the corolla opening).*—0.5–0.6 cm.

*Lateral lobes, width.*—0.9 cm.

*Lower lobe, length (from the corolla opening).*—1.3 cm.

*Lower lobe, width.*—1.6 cm.

Spur: Funnel-shaped and downwards directed

*Spur length.*—0.7–0.8 cm.

*Spur diameter.*—0.25 cm at upper end.

*Spur color.*—(Initially) mainly RHS 51B, dull pink, turning dull purple, RHS 186B (base) to RHS 186C (tip) with maturity.

Flower bud:

*Shape.*—Initially a somewhat flattened half-sphere, oyster shape at opening.

*Width.*—0.7 cm.

*Length.*—0.5 cm.

*Color* (*at tight bud*).—Salmon-pink, RHS 37B–C.

Calyx:

*Form.*—5 sepals, slanting downwards.

*Sepal color.*—RHS 143A on both sides.

*Length.*—0.2–0.3 cm.

*Width.*—0.2 cm.

*Shape.*—Deltoid to lanceolate.

*Apex.*—Acute.

*Base.*—Fused.

*Texture, upper surface.*—Glabrous.

*Texture, lower surface.*—Covered with glandular hair.

Pedicels:

*Color.*—RHS 144A near base to 144B at flower end.

*Length.*—1.0–1.7 cm.

*Diameter.*—0.1 cm.

*Texture.*—Dense hair, hirsute, partly glandular hair.

Reproductive organs:

Stamens:

*Quantity and arrangement.*—4; coherent, arching towards and somewhat twisting around the pistil.

*Filament, color.*—RHS 63B near anther, lighter towards base.

*Length.*—0.3–0.4 cm.

*Diameter.*—0.1 cm.

*Anther color.*—RHS 11A, yellow.

*Pollen amount.*—Abundant.

*Pollen color.*—RHS 12A.

Pistil:

*Quantity per flower.*—One.

*Length.*—0.3–0.4 cm.

*Stigma color.*—RHS 154A.

*Style color.*—RHS 145B.

Fruit and seed set: Has not been observed

Disease and insect resistance: Resistance and susceptibility typical for the species; no special observations made.

What is claimed is:

1. A new and distinct variety of *Diascia* plant named 'Dala Oran,' substantially as illustrated and described herein.

* * * * *

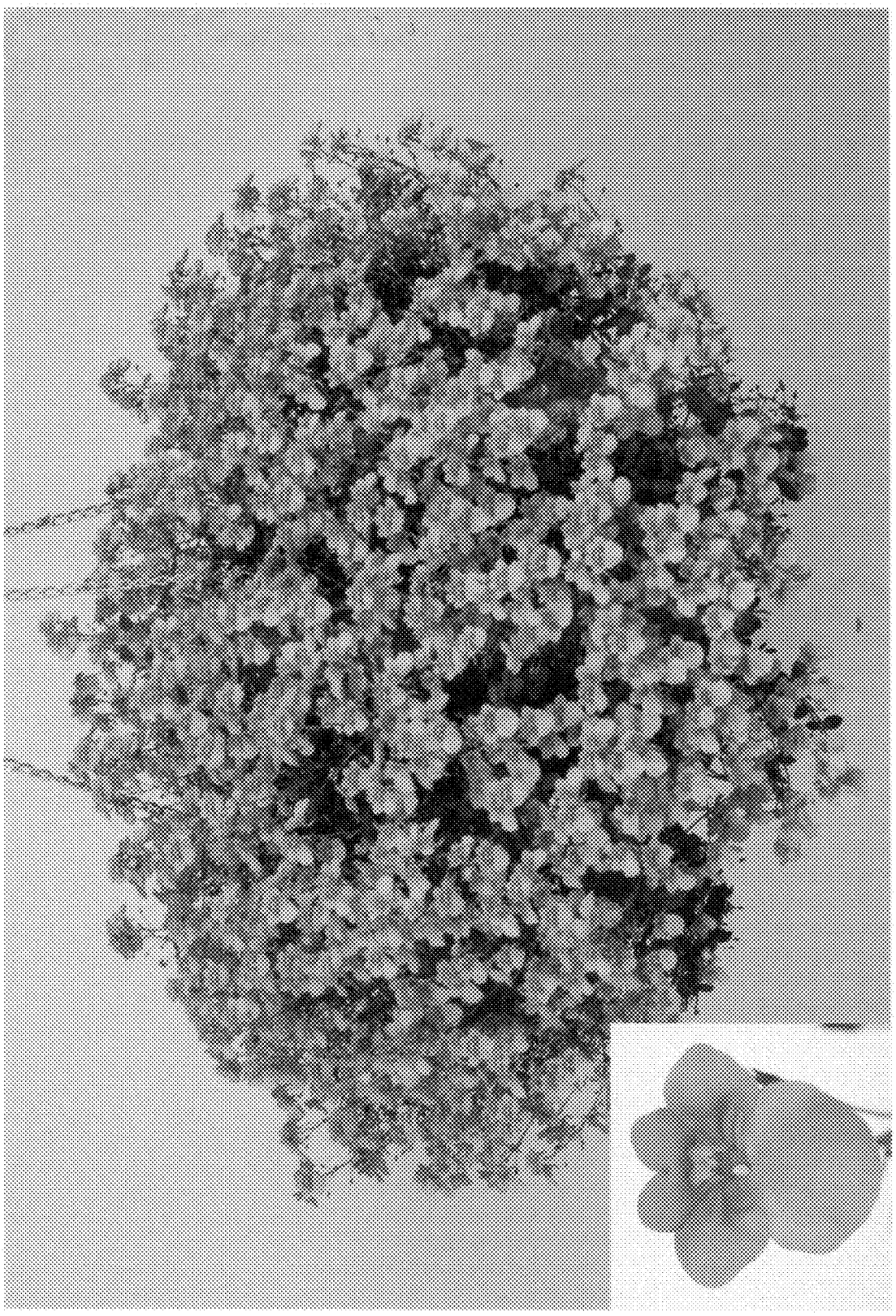

UNITED STATES PATENT AND TRADEMARK OFFICE

CERTIFICATE OF CORRECTION

PATENT NO. : PP 20,905 P2
APPLICATION NO. : 12/315293
DATED : March 30, 2010
INVENTOR(S) : Eric Giesen It is certified that error appears in the above-identified patent and that said Letters Patent is hereby corrected as shown below:

At column 1, lines 24-25, delete "'Data Oran'" and insert therefor --'Dala Oran'--

Signed and Sealed this

Eleventh Day of May, 2010

David J. Kappos

David J. Kappos
*Director of the United States Patent and Trademark Office*